US008419795B2

(12) United States Patent
Sweeney

(10) Patent No.: US 8,419,795 B2
(45) Date of Patent: Apr. 16, 2013

(54) INTERBODY CAGE SYSTEM

(75) Inventor: Patrick J. Sweeney, Flossmoor, IL (US)

(73) Assignee: Spinal Generations, LLC, Mokena, IL (US)

( * ) Notice: Subject to any disclaimer, the term of this patent is extended or adjusted under 35 U.S.C. 154(b) by 492 days.

(21) Appl. No.: 12/482,329

(22) Filed: Jun. 10, 2009

(65) Prior Publication Data
US 2009/0248164 A1 Oct. 1, 2009

Related U.S. Application Data

(63) Continuation of application No. 11/340,369, filed on Jan. 26, 2006, now Pat. No. 7,588,599.

(51) Int. Cl.
*A61F 2/44* (2006.01)
(52) U.S. Cl.
USPC .................................. 623/17.11; 623/17.12
(58) Field of Classification Search .......... 606/246–249, 606/90, 99, 105; 623/17.11–17.16
See application file for complete search history.

(56) References Cited

U.S. PATENT DOCUMENTS

| | | | |
|---|---|---|---|
| 4,016,863 A | 4/1977 | Brantigan |
| 4,743,256 A | 5/1988 | Brantigan |
| 4,834,757 A | 5/1989 | Brantigan |
| 4,878,915 A | 11/1989 | Brantigan |
| 5,015,247 A | 5/1991 | Michelson |
| 5,192,327 A | 3/1993 | Brantigan |
| 5,425,772 A | 6/1995 | Brantigan |
| 5,645,598 A | 7/1997 | Brosnahan, III |
| 5,665,122 A | 9/1997 | Kambin |
| 5,766,253 A | 6/1998 | Brosnahan, III |
| 5,865,847 A | 2/1999 | Kohrs et al. |
| 6,080,158 A | 6/2000 | Lin |
| 6,090,143 A | 7/2000 | Meriwether et al. |
| 6,096,080 A | 8/2000 | Nicholson et al. |
| 6,102,948 A | 8/2000 | Brosnahan, III |
| 6,123,705 A | 9/2000 | Michelson |
| 6,149,686 A | 11/2000 | Kuslich et al. |
| 6,159,245 A | 12/2000 | Meriwether et al. |
| 6,224,595 B1 | 5/2001 | Michelson |
| 6,241,733 B1 | 6/2001 | Nicholson et al. |
| 6,241,769 B1 | 6/2001 | Nicholson et al. |
| 6,258,094 B1 | 7/2001 | Nicholson et al. |
| 6,261,293 B1 | 7/2001 | Nicholson et al. |
| 6,261,295 B1 | 7/2001 | Nicholson et al. |
| 6,267,763 B1 | 7/2001 | Castro |
| 6,290,724 B1 | 9/2001 | Marino |
| 6,312,431 B1 | 11/2001 | Asfora |
| 6,488,710 B2 | 12/2002 | Besselink |
| 6,530,955 B2 | 3/2003 | Boyle et al. |
| 6,576,016 B1 | 6/2003 | Hochshuler et al. |
| 6,582,431 B1 | 6/2003 | Ray |
| 6,679,887 B2 | 1/2004 | Nicholson et al. |
| 6,743,255 B2 | 6/2004 | Ferree |
| 6,800,093 B2 | 10/2004 | Nicholson et al. |
| 6,805,697 B1 | 10/2004 | Helm et al. |
| 6,827,743 B2 | 12/2004 | Eisermann et al. |
| 6,942,697 B2 | 9/2005 | Lange et al. |

(Continued)

*Primary Examiner* — Eduardo C Robert
*Assistant Examiner* — Tara Carter
(74) *Attorney, Agent, or Firm* — Foley & Lardner LLP

(57) ABSTRACT

An interbody cage system includes an interbody cage having a proximal end, a distal end, and an interior. The interbody cage system also includes an insertion tool. A portion of the insertion tool extends into the proximal end and the interior.

7 Claims, 18 Drawing Sheets

U.S. PATENT DOCUMENTS

| | | |
|---|---|---|
| 7,320,686 B2 | 1/2008 | Serhan et al. |
| 7,655,010 B2 | 2/2010 | Serhan et al. |
| 2002/0032483 A1 | 3/2002 | Nicholson et al. |
| 2002/0123750 A1 | 9/2002 | Eisermann et al. |
| 2003/0097136 A1 | 5/2003 | Hajianpour |
| 2003/0153975 A1 | 8/2003 | Byrd, III et al. |
| 2003/0232065 A1 | 12/2003 | Remington et al. |
| 2003/0233147 A1 | 12/2003 | Nicholson et al. |
| 2004/0006125 A1 | 1/2004 | Remington et al. |
| 2004/0186572 A1 | 9/2004 | Lange et al. |
| 2004/0215202 A1 | 10/2004 | Preissman |
| 2005/0038514 A1 | 2/2005 | Helm et al. |
| 2005/0043733 A1 | 2/2005 | Eisermann et al. |
| 2005/0070900 A1* | 3/2005 | Serhan et al. .................. 606/61 |
| 2005/0071013 A1* | 3/2005 | Zubok et al. ............... 623/17.16 |
| 2005/0119747 A1 | 6/2005 | Fabris Monterumici et al. |
| 2005/0246021 A1 | 11/2005 | Ringeisen et al. |
| 2005/0273166 A1 | 12/2005 | Sweeney |

\* cited by examiner

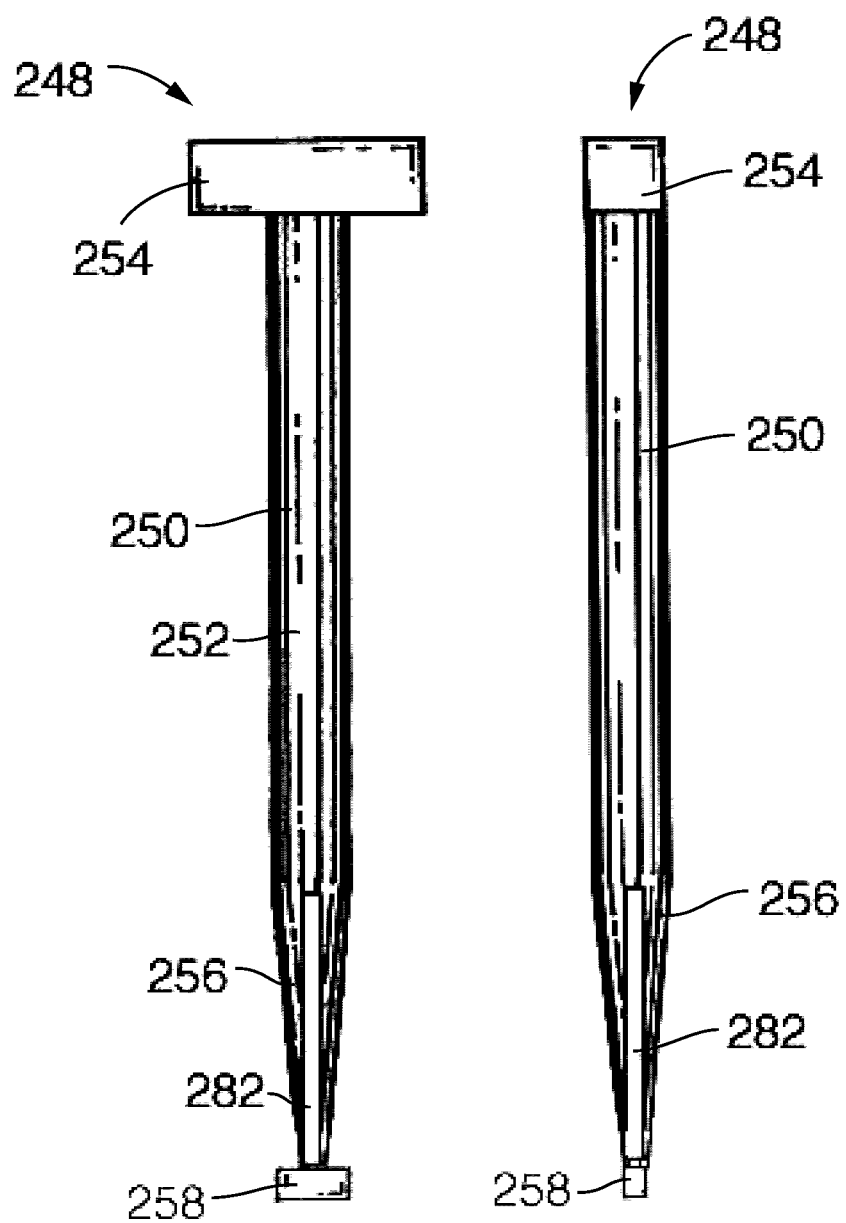

INTERBODY CAGE SYSTEM

CROSS-REFERENCE TO RELATED PATENT APPLICATIONS

This is a continuation of application Ser. No. 11/340,369, filed Jan. 26, 2006, which is incorporated herein by reference in its entirety.

FIELD OF THE INVENTION

The present invention relates to instrumentation and methods used in the installation of orthopedic implants used to facilitate bone growth and stabilize adjacent vertebrae as a part of spinal fusion procedures. In particular, the present invention relates to an interbody cage system and related surgical methods.

BACKGROUND OF THE INVENTION

The spinal column is comprised of twenty-six interlocking vertebrae. These vertebrae are separated by disks. The spine provides load-bearing support for one-half of the body's mass and it protects the nerves of the spinal column. The disks provide shock absorption and facilitate the bending of the spine.

The combination of the vertebrae and disks at each vertebral segment allows for motion of the spine, in particular, flexing, rotation, and extension. The motion and support functions of the spine, in combination with the many interlocking parts and nerve roots associated with the spinal column, can result in back pain due to various reasons. Such back pain may result from the degeneration of disks due to age, disease, or injury. Further, vertebral bodies may be compromised due to disease or defect, such as a tumor, or injury, such as fracture.

Spinal fusion surgery is one way to treat back pain. Further, spinal fusion may be used to correct an abnormal curvature of the spine or stabilize the spine due to injury or disease affecting one or more disks or vertebrae. In a spinal fusion procedure, two or more adjacent vertebrae in the spine are fused together. Typically, bone graft material or a suitable substitute is utilized to aid in the creation of bone structure between the fused vertebrae to create a single bone. In order to facilitate the placement of the bone graft material and the fusion of the bone graft material to the adjoining vertebrae, disk material is removed between the vertebrae, and one or more spinal implants, or interbody cages, are installed. The typical interbody cage is a porous cylindrical device, having a closed circumference and an interior volume. Interbody cages may be manufactured from titanium, plastic, reinforced plastic, or other suitable material. The cage is typically packed with bone graft material with the intent that bone growth will be stimulated within and around the cage and the two vertebral bodies will fuse together.

One challenge associated with spinal fusion procedures is maintaining proper separation between the vertebrae to be fused during and after surgery. Ideally, an interbody cage should provide adequate support and stability to the surrounding vertebral bodies during the fusion process.

Ideally, an interbody cage system should also be configured for use in a minimally invasive surgical approach requiring a smaller percutaneous aperture. Further, it would be advantageous for an interbody cage system to require fewer surgical tools and/or devices to be used during the procedure.

An additional challenge is distracting the adjacent vertebrae to the proper separation during insertion of the cage. Ideally, an interbody cage should be configured for easy insertion and self-distraction.

An additional challenge is the ability to deliver fluids to the disk space once the cage is installed. Ideally an interbody cage system should facilitate the delivery of fluids, including various types of viscous fluids, to the disk space during spinal fusion procedures.

An additional challenge is the ability to easily remove an interbody cage. Ideally, an interbody cage system should provide for easy removal of an interbody cage where removal is desired and/or necessary.

It would be desirable to provide a system and/or method that provides one or more of these or other advantageous features or addresses one or more of the above-identified needs. Other features and advantages will be made apparent from the present specification. The teachings disclosed extend to those embodiments that fall within the scope of the appended claims, regardless of whether they accomplish one or more of the above-identified needs.

SUMMARY OF THE INVENTION

The invention relates to an interbody cage system including an interbody cage having a proximal end, a distal end, and an interior. The interbody cage system further includes an insertion tool, wherein a portion of the insertion tool extends into the proximal end and the interior.

The invention further relates to an interbody cage instrumentation kit including an interbody cage having a proximal end and a distal end and an insertion tool, wherein the interbody cage includes a pair of insertion surfaces extending from the proximal end to the distal end and tapering toward each other in a first direction, and a pair of gripping surfaces extending from the proximal end to the distal end and tapering toward each other in a second direction, wherein the first direction is opposite that of the second direction.

The invention further relates to a method for inserting an interbody cage into a disk space between a first vertebra and a second vertebra. The method includes the steps of opening an aperture in a patient to allow access to the disk space and the first vertebra and the second vertebra, providing an interbody cage, inserting the interbody cage into the disk space wherein the first vertebra and the second vertebra are distracted a first distance, and rotating the interbody cage within the disk space wherein the first vertebra and the second vertebra are distracted a second distance.

The invention further relates to an interbody cage having a distal surface located at the distal end of the interbody cage, a pair of proximal surfaces located at a proximal end of the cage, a pair of insertion surfaces extending from the distal surface to the pair of proximal surfaces, and a pair of gripping surfaces extending from the distal surface to the pair of proximal surfaces. A first distance measured between the pair of insertion surfaces at the proximal end is greater than a second distance measured between the pair of insertion surfaces at the distal end, and a third distance measured between the pair of gripping surfaces at the proximal end is less than a fourth distance measured between the gripping surfaces at the distal end.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which:

FIG. 17 is a front elevation view of an insertion tool;

FIG. 18 is a side elevation view of the insertion tool of FIG. 17;

DETAILED DESCRIPTION OF THE PREFERRED EMBODIMENTS

Referring to FIGS. 1-5, in an exemplary embodiment of the invention, an interbody cage system includes an implantable device, shown as an interbody cage 10, and an insertion tool 48. The insertion tool 48, as discussed in further detail herein, is intended to couple with interbody cage 10 and facilitate the insertion and manipulation of interbody cage 10 during surgical procedures.

Figure 1:
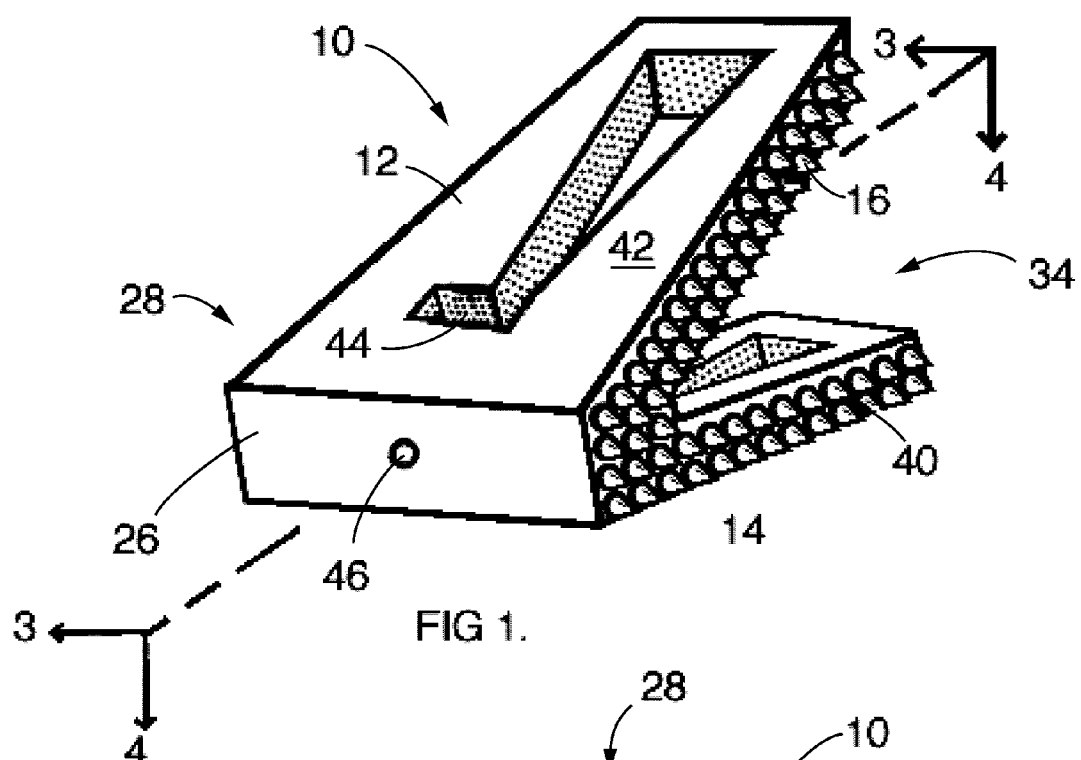
FIG. 1 is a perspective view of an interbody cage viewed from the distal end.
Figure 2:
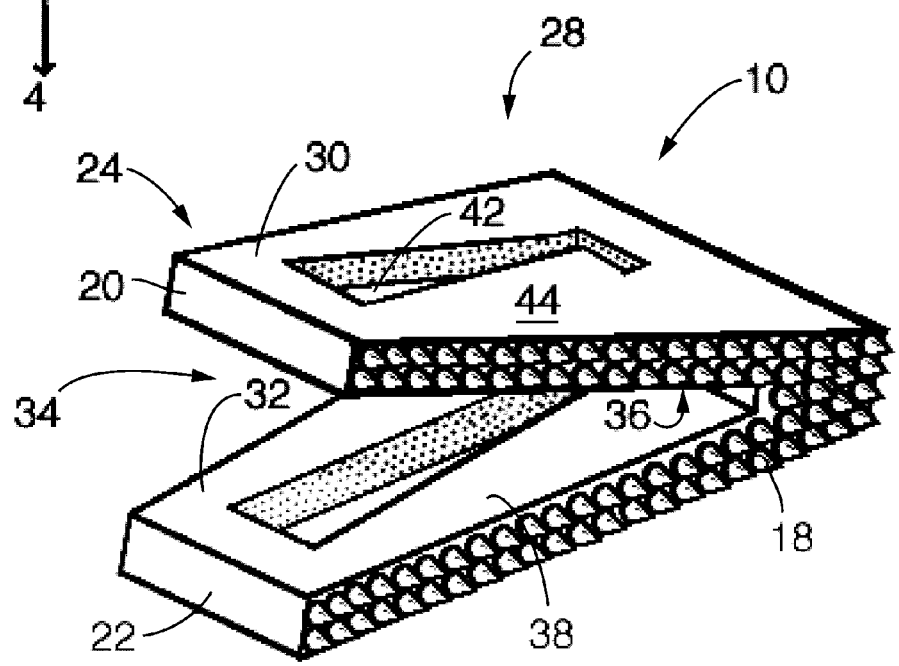
FIG. 2 is a perspective view of the interbody cage of FIG. 1 viewed from the proximal end.

Referring to FIGS. 1 and 2, interbody cage 10 has two insertion surfaces 12, 14 and two gripping surfaces 16, 18. The insertion surfaces 12, 14 and the gripping surfaces 16, 18 extend from a pair of proximal faces 20, 22 located at a proximal end 24 of cage 10 to a distal face 26 located at a distal end 28 of cage 10. As shown in FIGS. 1 and 2, gripping surfaces 16, 18 and insertion surfaces 12, 14 extend along a pair of extensions 30, 32 that project outward, forming a "V" shape such that cage 10 has an interior area 34 between the inner surfaces 36, 38 of extensions 30, 32. The "V" shape provides a taper such that the distance between the two insertion surfaces 12, 14 is greater at the proximal end 24 of cage 10 than at the distal end 28 of cage 10. This tapered configuration facilitates the insertion of cage 10 and the initial distraction of the two adjoining vertebral bodies 62, 64 (see FIG. 7) during surgical procedures, as disclosed herein and discussed further below.

Further referring to FIGS. 1 and 2, in addition to the first taper between insertion surfaces 12, 14, cage 10 is also tapered between gripping surfaces 16, 18 such that the distance between gripping surfaces 16, 18 is less at the proximal end 24 of cage 10 than at the distal end 28 of cage 10. As discussed in further detail below, this second taper facilitates secondary distraction of the vertebral bodies 62, 64 during and after rotation of cage 10 into its final position, and may be configured such that cage 10 maintains the natural curvature of the spine in a specific area, shown and discussed herein as the lumbar region.

While only one embodiment of the types of tapers that may be used as a part of interbody cage 10 is disclosed in the Figures, it should be understood that the dimensions and configurations of one or both of the tapers may be modified to adapt interbody cage 10 for usage in any suitable region of the spine and to allow initial insertion of cage 10 with minimal effort and to provide proper longer-term distraction of the vertebral bodies 62, 64 after surgical procedures and during the fusion process.

Figure 3:
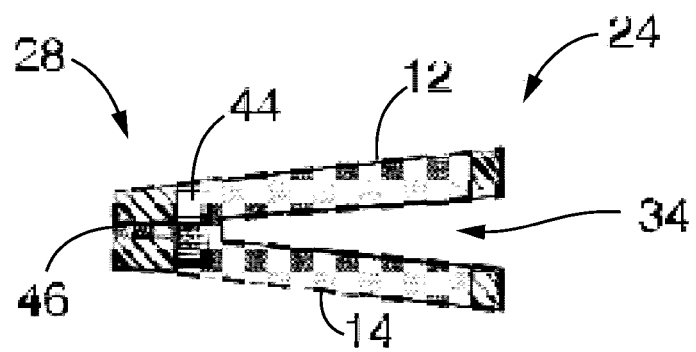
FIG. 3 is a sectional view of the interbody cage of FIG. 1, taken generally along line 3-3 of FIG. 1.
Figure 4:
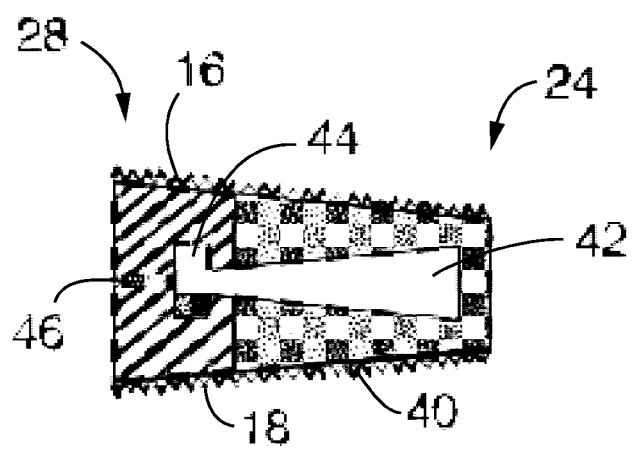
FIG. 4 is a sectional view of the interbody cage of FIG. 1, taken generally along line 4-4 of FIG. 1.
Figure 9:
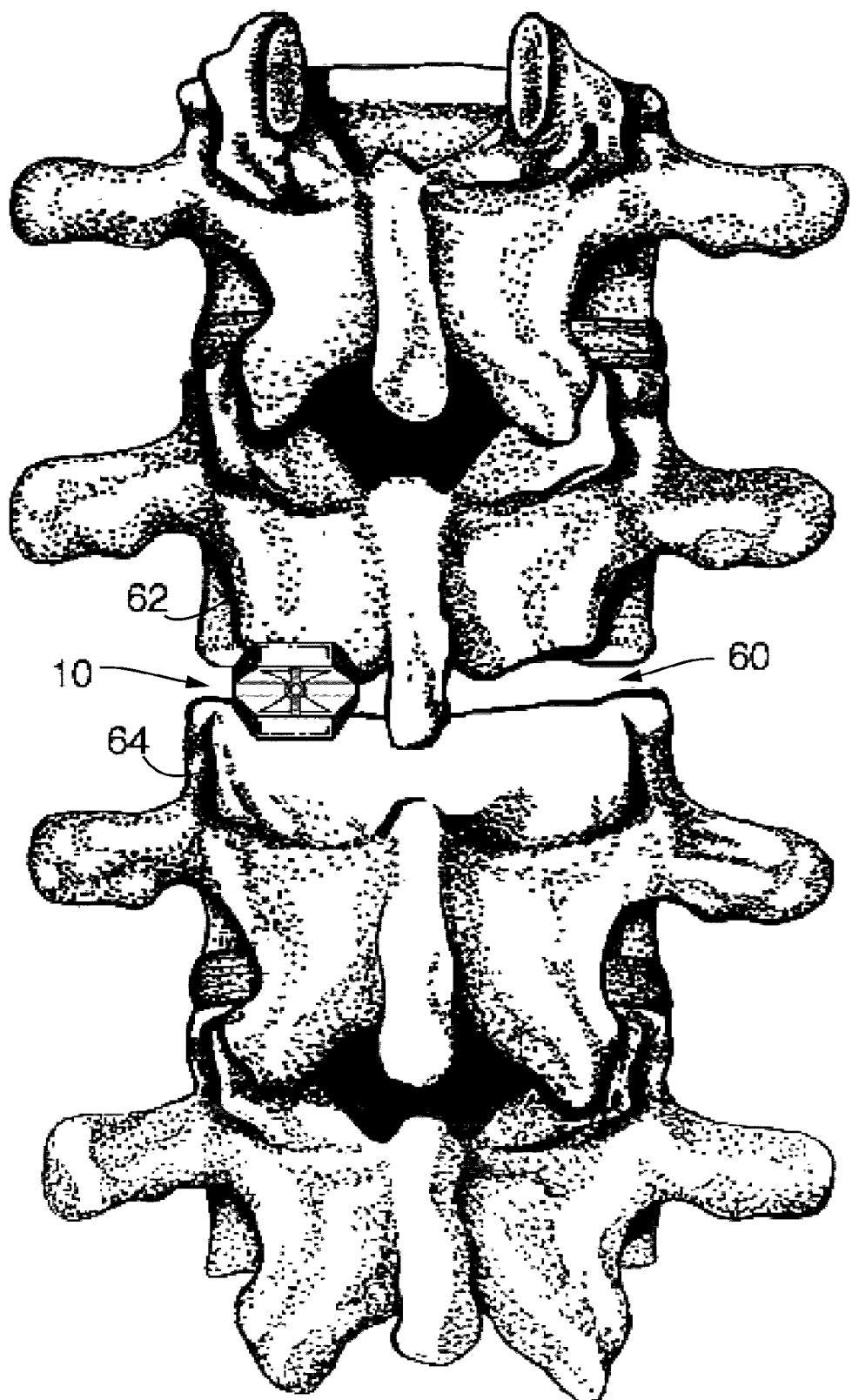
FIG. 9 is a rear elevation view of an interbody cage prior to rotation, shown with a disk space.

Referring to FIGS. 3 and 4, insertion surfaces 12, 14 are shown as substantially smooth surfaces, intended to allow easy insertion and positioning of cage 10 within the intervertebral space or disk space 60 (see FIG. 9). Once properly positioned, as discussed below, cage 10 is rotated approximately 90 degrees about the longitudinal axis of the tool 48 such that each of gripping surfaces 16, 18 contacts and facially interfaces with one of vertebral bodies 62, 64 within the intervertebral space 60 (see FIG. 10). The gripping surfaces 16, 18 are provided with gripping members, or protrusions 40 (e.g., teeth, ridges, nubs, spikes, etc.), configured to provide stability to cage 10 by gripping vertebral bodies 62, 64 and preventing movement of cage 10 once it is properly positioned and rotated into place.

Figure 5:
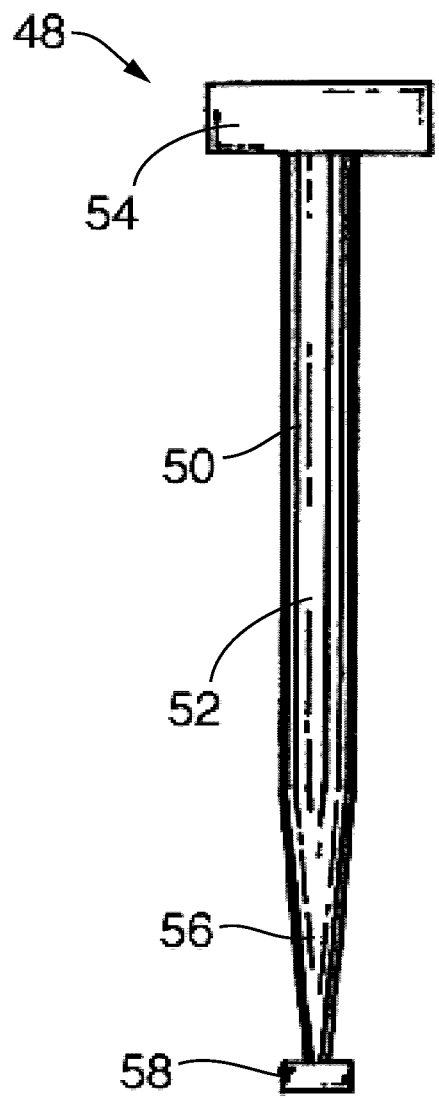
FIG. 5 is a front elevation view of an insertion tool.

Further referring to FIGS. 1-4, interbody cage 10 has an aperture 42 extending between insertion surfaces 12, 14. Aperture 42 is tapered, being wider at the proximal end 24 than the distal end 28, to allow clearance for the insertion of tool 48. Aperture 42 has a keyed portion 44 at the distal end of aperture 42 configured to receive the distal end of tool 48 and provide for rotation of interbody cage 10 via rotation of tool 48. Aperture 42 extends into extensions 30, 32 of cage 10, thereby allowing communication between the interior area 34 of cage 10 and the disk space 60 upon installation of cage 10. This communication is intended to facilitate bone ingrowth in and around cage 10, and to allow the delivery of fluids, including various viscous fluids, to the entire disk space 60 via tool 48, as discussed further below. As shown in FIGS. 3-5, keyed portion 44 of aperture 42 is configured to receive a keyed segment 58 of tool 48, and upon an approximately 90 degree rotation of tool 48, secure tool 48 within cage 10 so as to prevent further rotation in the same direction and to prevent distal or proximal movement of tool 48 relative to cage 10. The taper of aperture 42, conforming to a tapered portion 56 of tool 48, additionally restrains tool 48 within cage 10 and is intended to prevent lateral movement of the tool 48 relative to cage 10 once tool 48 is installed.

Further referring to FIGS. 1-4, interbody cage 10 may include a hole 46 that extends from the distal end of aperture 42 to distal face 26 of interbody cage 10. Hole 46 may be threaded to secure a threaded portion of an internal screw 172 (see FIG. 14) and provide additional stability to the interface of cage 10 and tool 48, as discussed further herein. In an alternative embodiment (not shown), cage 10 is provided without hole 46 and tool 48 is held in place by keyed portion 44 of aperture 42. Additionally, hole 46 may be provided as unthreaded and used, for example, as an additional means of communication between the interior portion 34 of cage 10 and the remainder of the intervertebral space 60.

Figure 6:
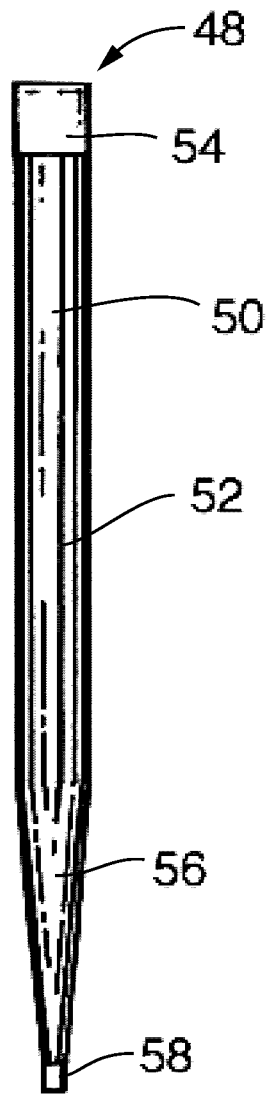
FIG. 6 is a side elevation view of the insertion tool of FIG. 5.

Referring to FIGS. 5 and 6, interbody cage 10 is intended to be used in conjunction with insertion tool 48. Insertion tool 48 includes a shaft 50 having a straight portion 52 and a tapered portion 56. Tool 48 has a handle 54 at the proximal end and a keyed segment 58 at the distal end. Tool 48 is intended to be coupled with interbody cage 10 prior to insertion of interbody cage 10 into intervertebral space 60. Keyed segment 58 of tool 48 locks into keyed portion 44 of aperture 42 such that cage 10 may be positioned and rotated within intervertebral space 60 via manipulation (e.g., lateral movement, rotation, etc.) of tool 48. The tapered portion 56 of tool 48 is configured to conform to the taper of aperture 42 to further prevent relative movement between tool 48 and the cage 10.

Figure 7:
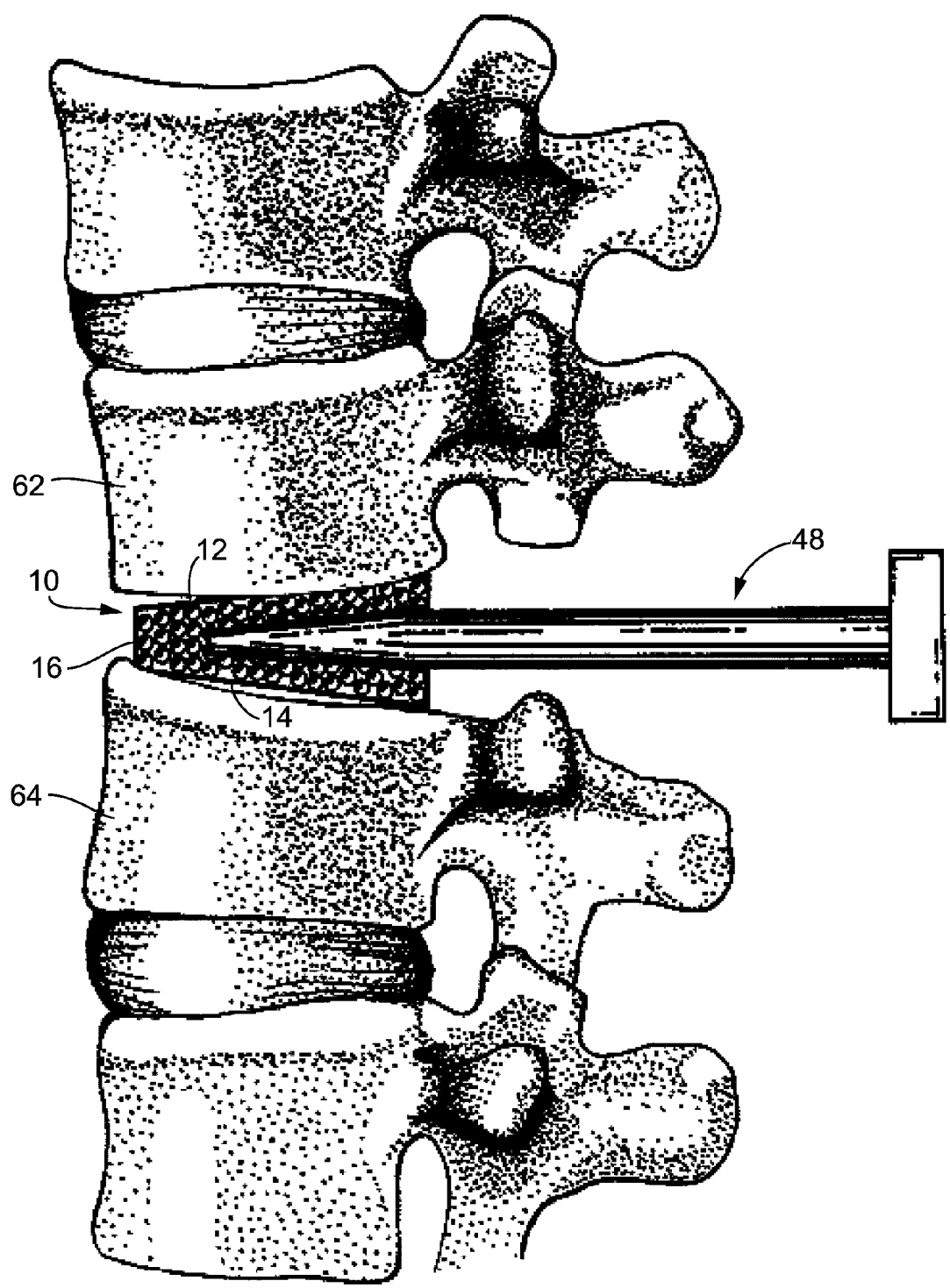
FIG. 7 is a side elevation view of an interbody cage prior to rotation, coupled to an insertion tool, shown within a disk space.
Figure 8:
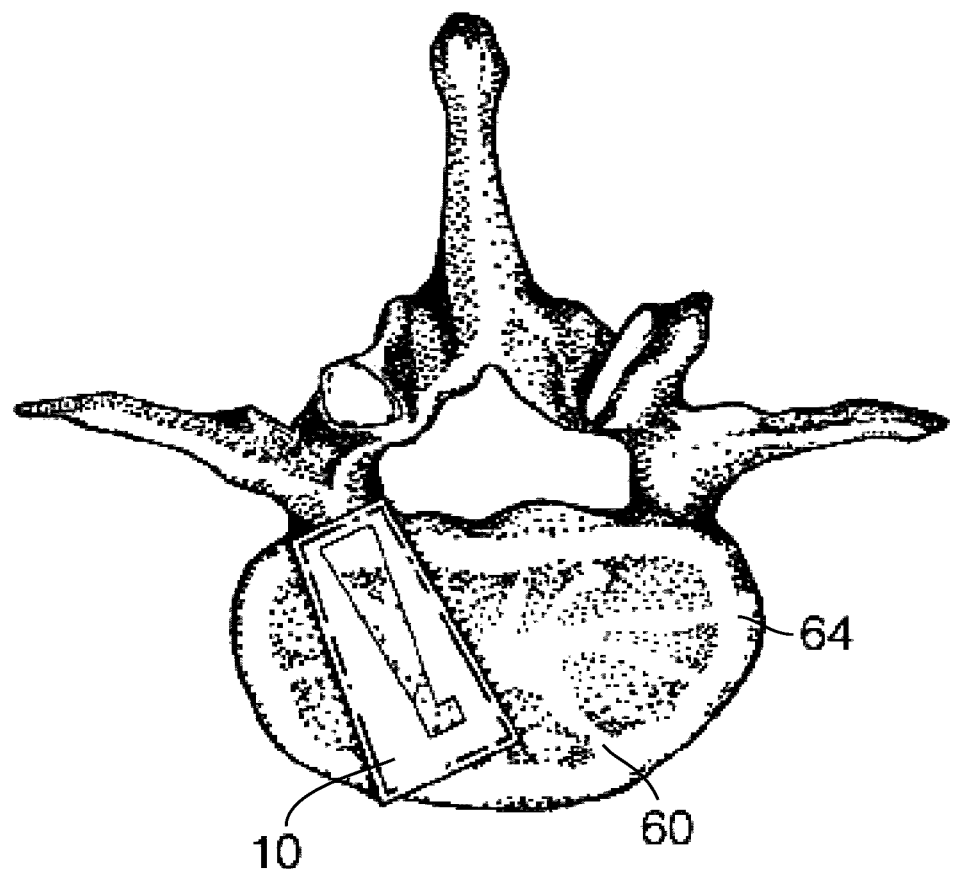
FIG. 8 is a top plan view of an interbody cage prior to rotation, shown within a disk space.
Figure 10:
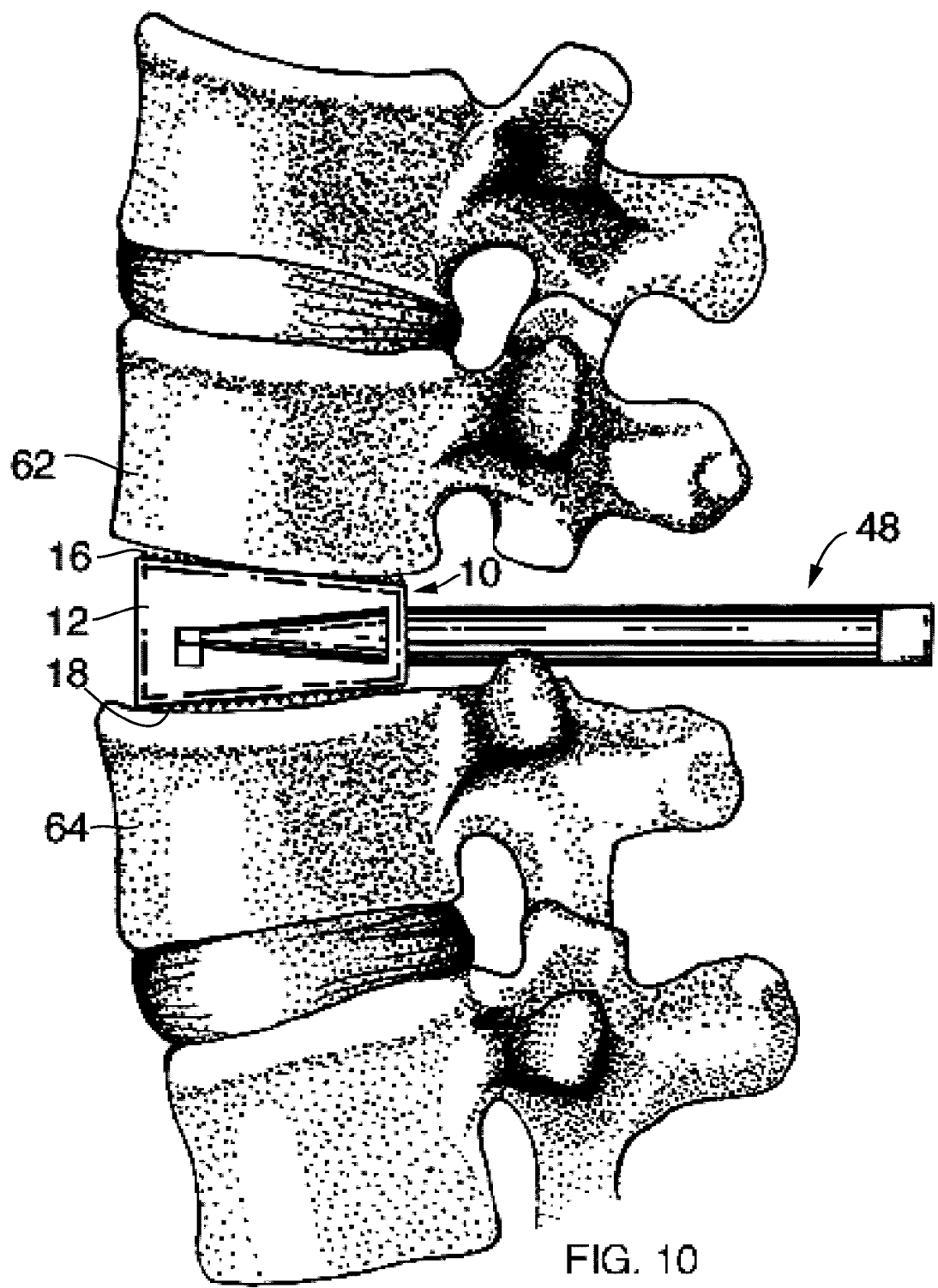
FIG. 10 is a side elevation view of the interbody cage of FIG. 9 coupled to the insertion tool of FIG. 9, after rotation of the interbody cage, shown within a disk space.
Figure 11:
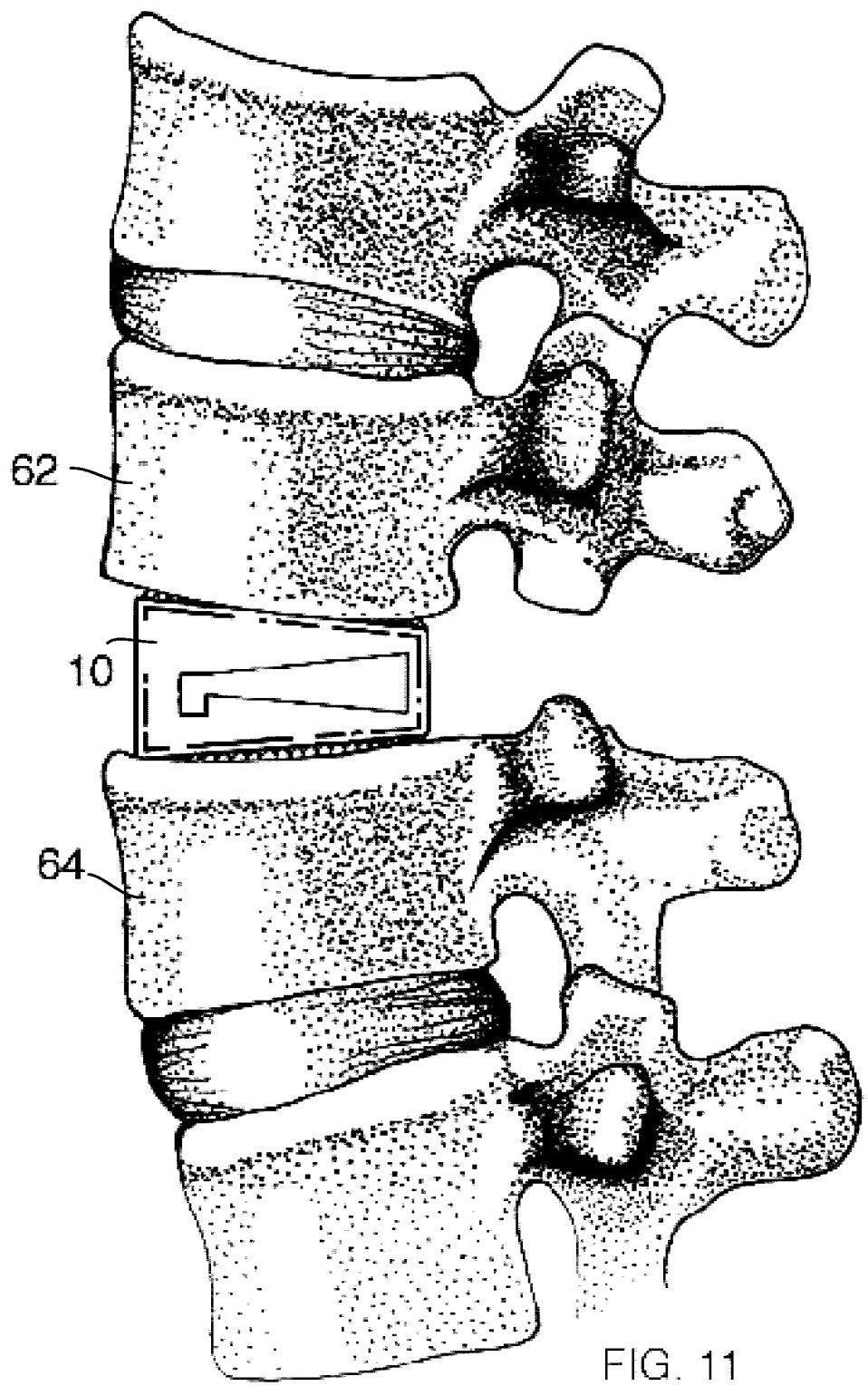
FIG. 11 is a side elevation view of the interbody cage of FIG. 9 after removal of the insertion tool, shown within a disk space.
Figure 12:
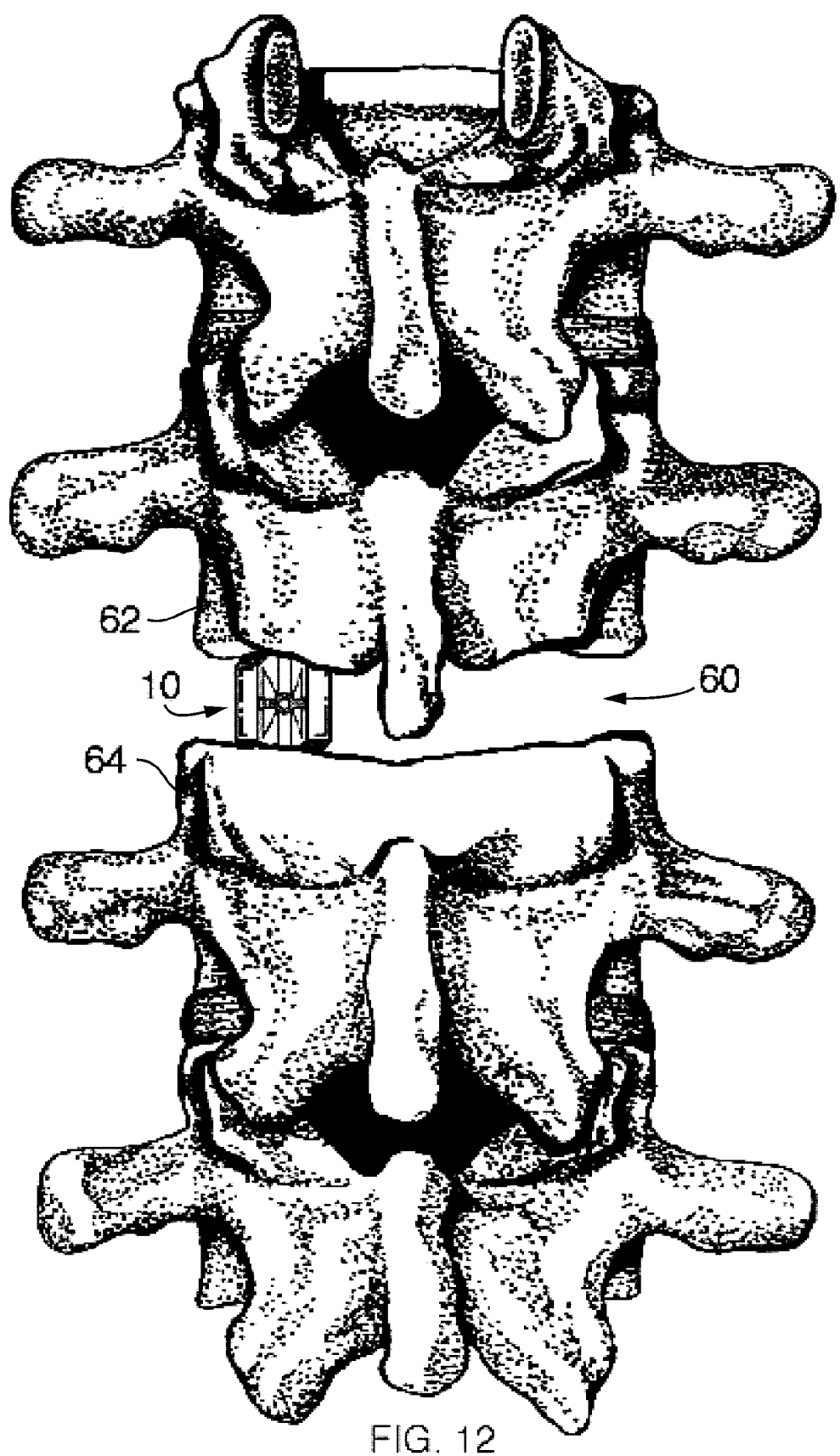
FIG. 12 is a rear elevation view of the interbody cage of FIG. 9 after removal of the insertion tool, shown within a disk space.

Referring to FIGS. 7-13, upon assembling tool 48 and interbody cage 10, the interbody cage 10 may be inserted into disk space 60 distal-face-first with the insertion surfaces 12, 14 facing each of the adjoining vertebral bodies 62, 64 (see FIGS. 7-9). The gradual increase in distance between insertion surfaces 12, 14 from the distal end 28 to the proximal end 24 allows a user to initially distract the adjoining vertebrae 62, 64 by applying an insertion force to tool 48 and inserting cage 10 into the proper position within the intervertebral space 60. As shown in FIGS. 10-12, once positioned, cage 10 may be rotated approximately 90 degrees so that gripping surfaces 16, 18 facially interface with vertebrae 62, 64 and secure cage 10 in place. The larger distance between gripping surfaces 16, 18 at the distal end 28 of cage 10 further distract vertebral bodies 62, 64 and conform cage 10 to the natural curvature of the spine. After properly installing and rotating cage 10, tool 48 may be rotated back 90 degrees (i.e., in a direction opposite to that used to lock the tool into the cage) and removed from the cage 10.

Figure 14:
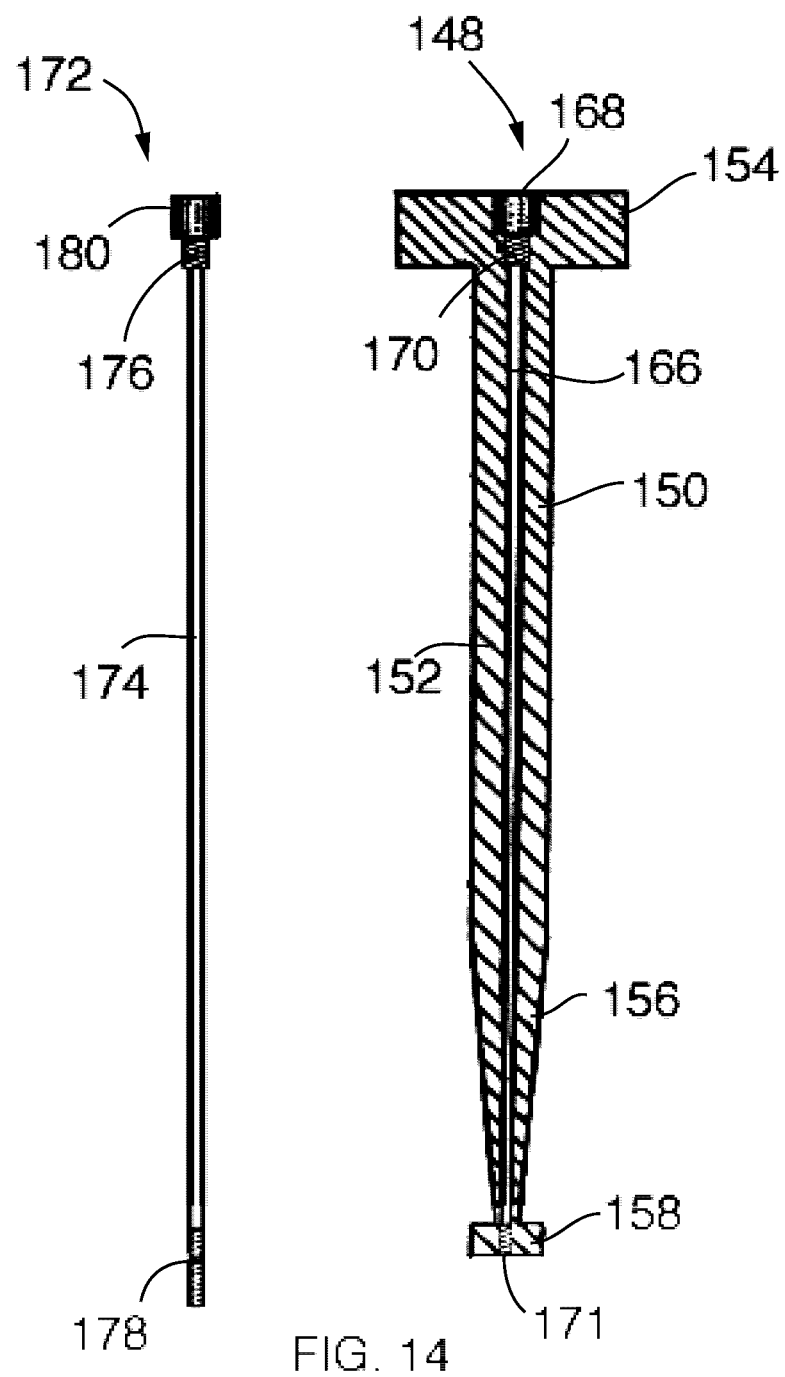
FIG. 14 is a sectional view of an interbody cage system.
Figure 15:
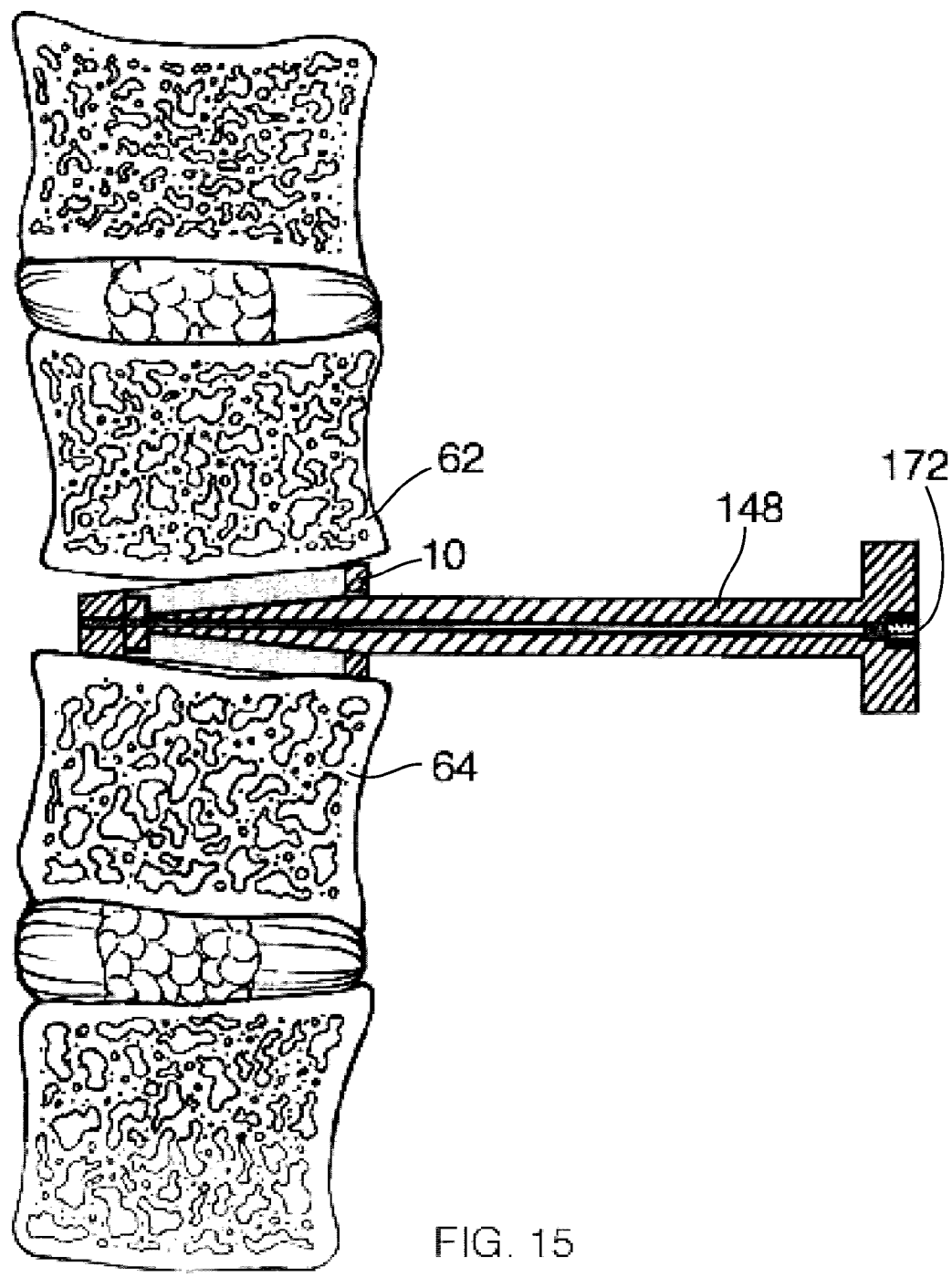
FIG. 15 is a sectional view of the interbody cage system of FIG. 14 with the internal screw coupled to the tool, prior to rotation of the interbody cage, shown within a disk space.
Figure 16:
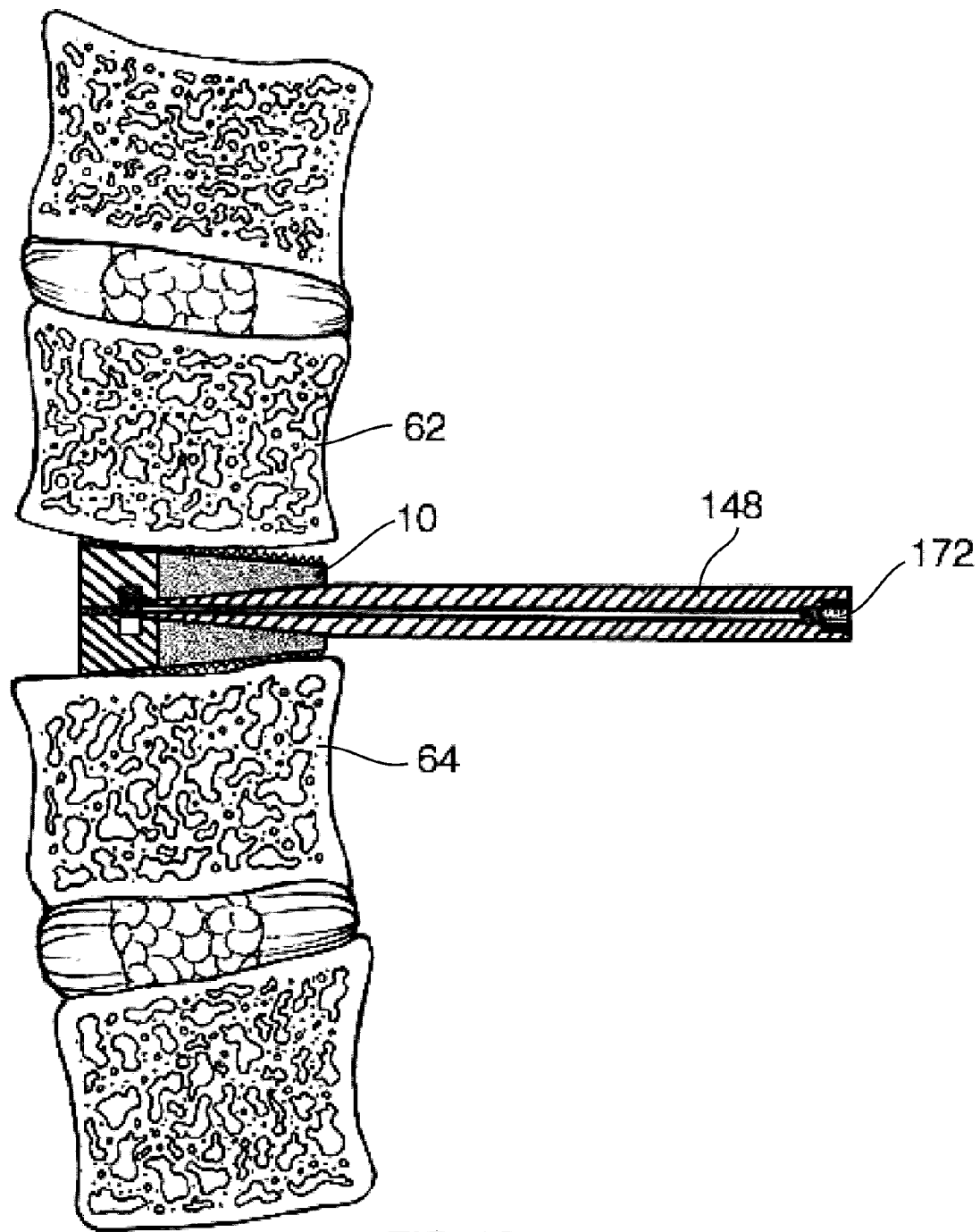
FIG. 16 is a sectional view of the interbody cage system of FIG. 14 after rotation of the interbody cage, shown within a disk space.
Figure 19:
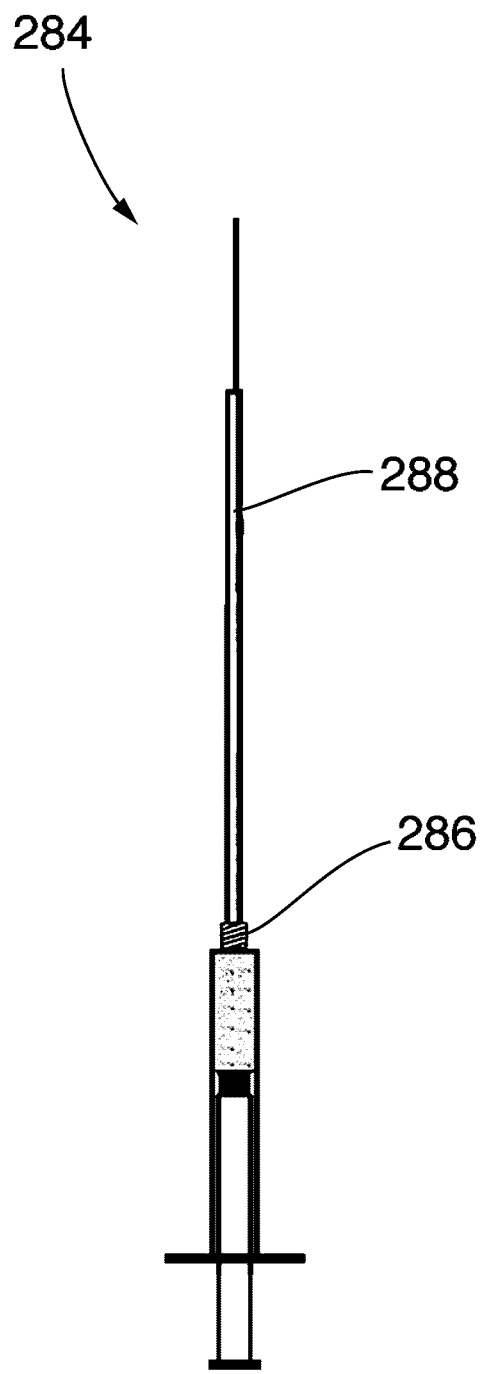
FIG. 19 is a front elevation view of a delivery device.

Referring to FIGS. 14-16, an interbody cage system according to another embodiment of the invention includes a cannulated tool 148 and an internal screw 172. Tool 148 is similar to tool 48 in that tool 148 includes a shaft 150 having a straight portion 152 and a tapered portion 156, a handle 154, and a keyed segment 158. Tool 148 additionally includes a passage 166 and a recess 168. Internal screw 172 is configured to be positioned within passage 166 of tool 148 and further secure tool 148 to cage 10 prior to installation of cage 10. As shown in FIG. 14, internal screw 172 has a screw shaft 174 with a proximal threaded portion 176 and a distal threaded portion 178. Additionally, screw 172 has a head 180 configured to fit within recess 168 in tool 148. Head 180 has a key (not shown) to allow screw 172 to be rotated within tool 148 and secured to both tool 148 and cage 10. When internal screw 172 is used with tool 148, cage 10 is provided with hole 46 having threads configured to receive the distal threaded portion 178, preventing movement between internal screw 172 and cage 10 once screw 172 is installed. In use, screw 172 is slid through passage 166 and distal threaded portion 178 is threaded into hole 46 of cage 10. As screw 172 and cage 10 are threaded together, head of 180 is captured within recess 168, thereby securing tool 148 to cage 10.

As discussed further below, tool 148 may be provided with a first threaded tool portion 170 and/or a second threaded tool portion 171. First threaded tool portion 170 may be configured to receive proximal threaded portion 176, and second threaded tool portion 171 may be configured to receive distal threaded portion 178 of screw 172. In an alternative embodiment, tool 148 may be provided without first threaded portion 170 and second threaded portion 171, and passage 166 may extend to recess 168. Tool 148 is held in place by head 180 of screw 172 engaging a shoulder provided between passage 166 and recess 168 in tool 148.

Referring to FIGS. 17-22, an interbody cage system according to another embodiment of the invention includes a fenestrated tool 248 intended to facilitate the delivery of fluids to a disk space. Tool 248 is similar to tool 148 in that tool 248 includes a shaft 250 having a straight portion 252 and a tapered portion 256, a handle 254, and a keyed segment 258. Tool 248 additionally includes a passage 266 and a recess 268, similar to those described with respect to tool 148. One or more openings 282 extend from passage 266 to the exterior surface of tool 248. Tool 248 is used in conjunction with delivery device 284, shown as a syringe, to provide for delivery of fluids to intervertebral space 60. As shown in FIGS. 17-20, tool 248 has one or more openings 282 located near the distal end of tool 248 so that when tool 248 is coupled with the cage 10, openings 282 in tool 248 are proximate aperture 42 in cage 10. This design allows the fluids to be delivered efficiently to the entire intervertebral space 60 after cage 10 has been installed. It should be understood that tool 248 and delivery device 284 may be used to deliver a wide variety of fluids. Examples of such fluids may include, among others, osteoconductive materials, osteoinductive materials, a slurry of biocompatible materials, resorbable culture mediums, tissue growth or differentiation factors (e.g., recombinant morphogenetic proteins, PDGF, TGF-.beta., EGF/TGF-.alpha., IGF-T, .beta.FGF, BMP(x), etc.), hydrogels, resorbable or nonresorbable synthetic or natural polymers (collagen, fibrin, polyglycolic acid, polylactic acid, polytetrafluoroethylene, etc.), antibiotics, anti-inflammatory medications, immunosuppressive medications, and various other fluids, viscous fluids, pastes, or similar substances.

Referring to FIGS. 17-20, the delivery device or syringe 284 includes a threaded syringe portion 286 configured to be threaded into threaded portion 270 of tool 248 and lock syringe 284 in place relative to tool 248. Syringe 284 has a shaft 288 with a distal end that extends to openings 282 when syringe 284 is threaded to tool 248, and provides for delivery of fluids via openings 282. According to an alternative embodiment, syringe 284 and tool 248 may be provided with mating internal and external threads at any suitable location (e.g., the distal end of tool 248 or the proximal end of syringe 284), or may be coupled together using other various methods known in the art.

Figure 20:
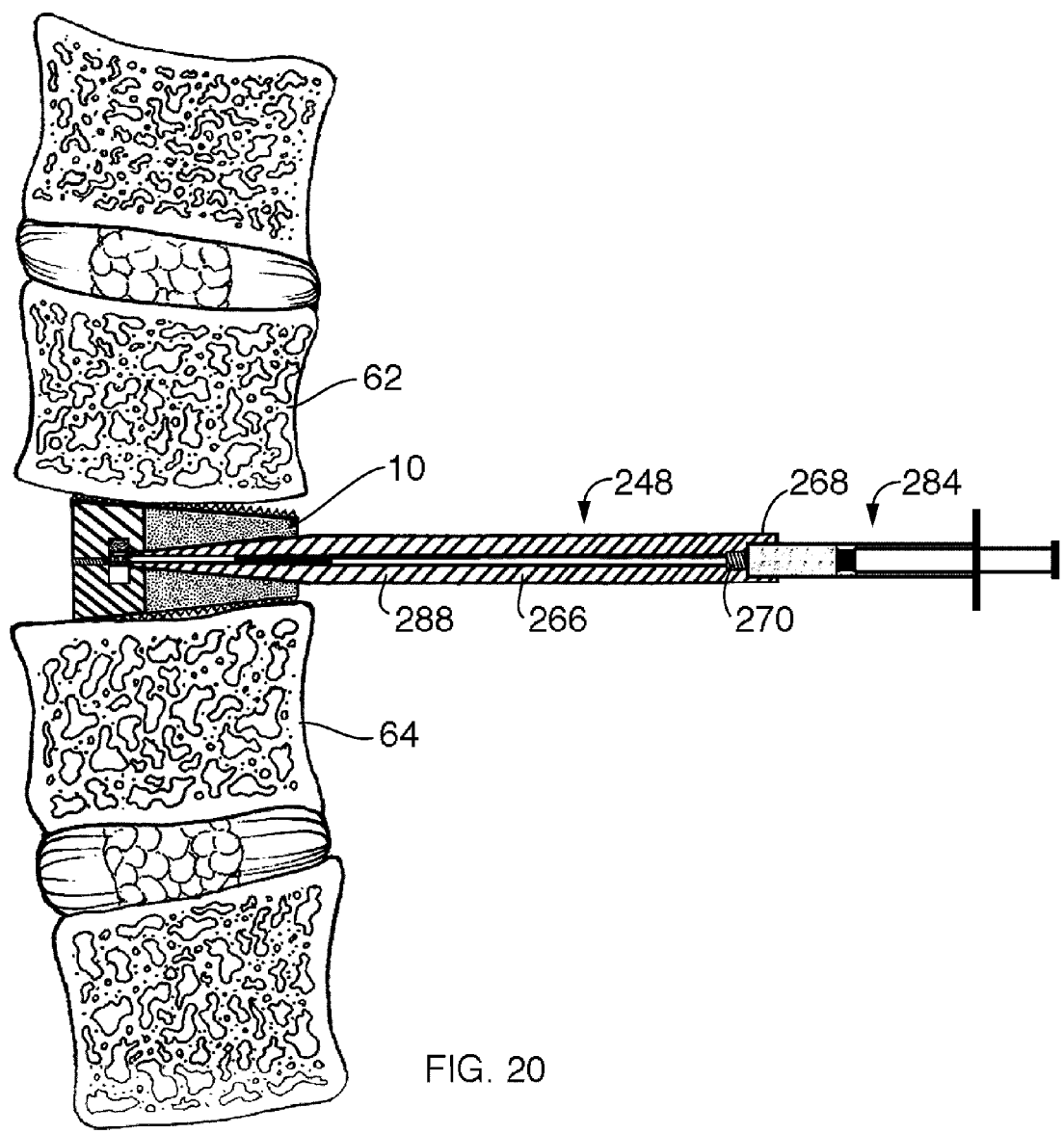
FIG. 20 is a sectional view of an interbody cage system having a delivery device, shown prior to delivery of fluids into a disk space.
Figure 21:
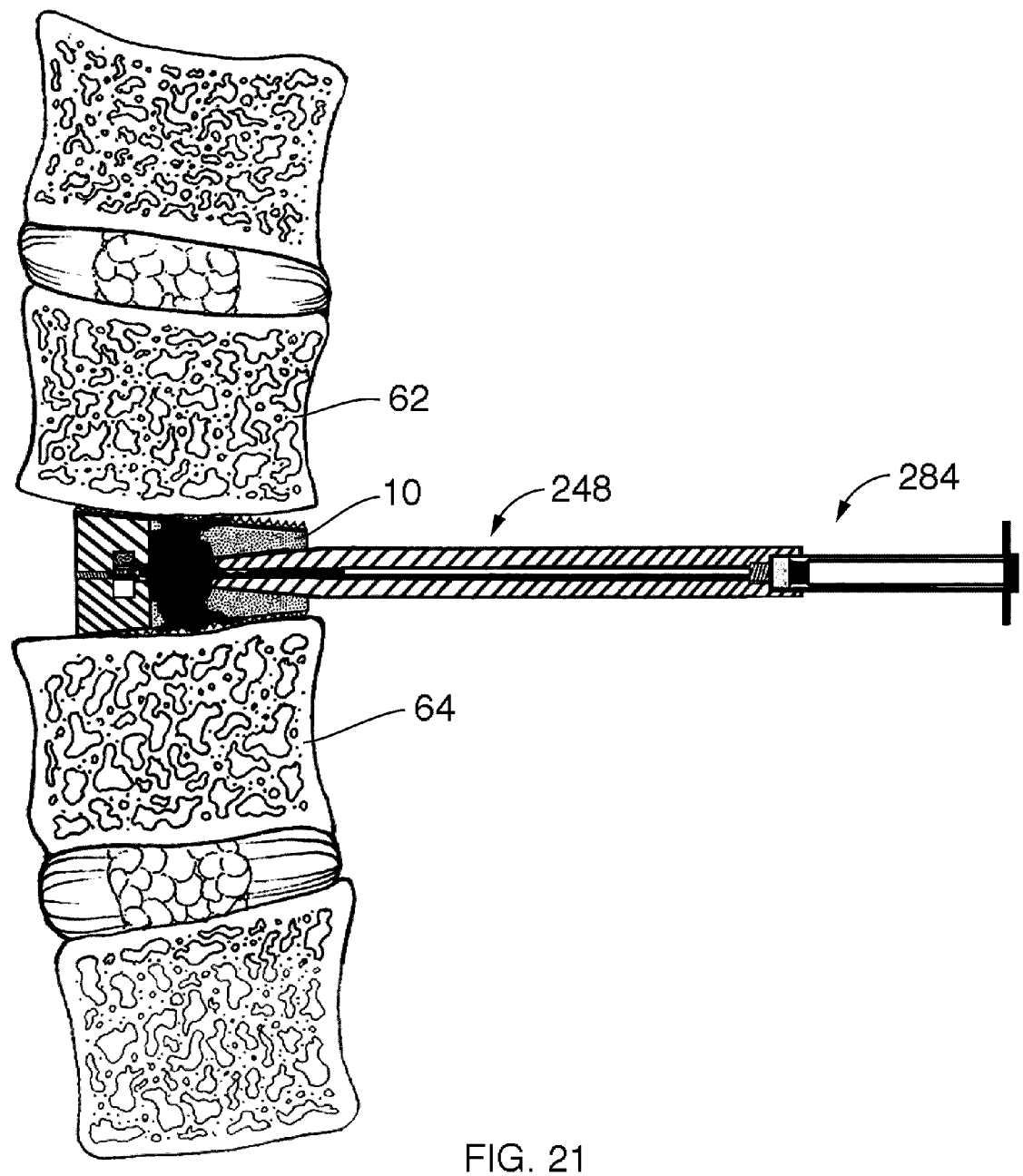
FIG. 21 is a sectional view of the interbody cage system of FIG. 20 having a delivery device, shown after delivery of fluids into the disk space.
Figure 22:
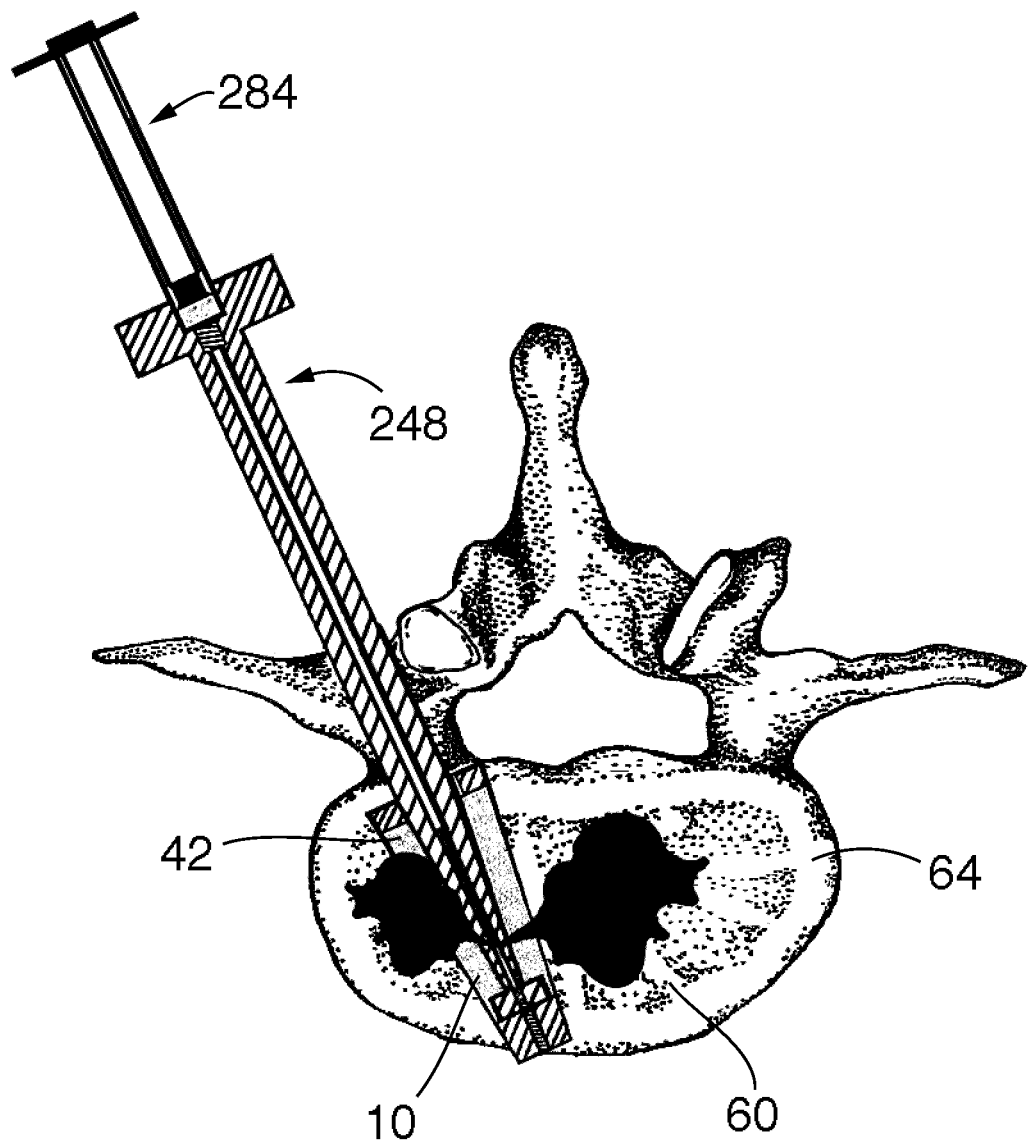
FIG. 22 is a sectional view of the interbody cage system of FIG. 20 having a delivery device, shown after delivery of fluids into the disk space.

Referring to FIGS. 20-22, in use, cage 10 is initially installed using any of the aforementioned methods. After proper positioning and rotation of cage 10, delivery device or syringe 284 is threaded into tool 248, and the fluids are delivered from delivery device 284, through openings 282 in tool 248, and into intervertebral space 60 where, as mentioned above and shown in FIG. 22, aperture 42 in cage 10 facilitates communication between the interior 34 of the cage 10 and the remaining portion of the intervertebral space 60.

The various interbody cage systems described herein as exemplary embodiments of the invention may be utilized in the performance of spinal fusion procedures using a method that is intended to simplify and shorten conventional spinal fusion procedures and provide advantages not available with the use of conventional systems and methodologies.

Prior to or during operating, imaging of the patient may be utilized to determine the proper configuration (e.g., the configuration of the tapers between the insertion and gripping surfaces) of interbody cage 10 to be used and the appropriate positions in which cage 10 is to be installed. An entry site is created in the patient's back along the portion of the spine to be treated. The spine and disk space are then exposed for treatment. The disk space 60 between vertebrae 62, 64 to be fused is then cleaned, leaving as much as possible of the disk annulus (not shown) in place to facilitate retaining the bone graft material and any fluids delivered to the area within the original disk space 60. Bone graft or a bone graft substitute may then be inserted, or packed, into a portion of disk space 60, leaving sufficient room for the insertion of one or more interbody cages 10.

With reference to the embodiment shown in FIGS. 7-13, after preparing disk space 60 for receipt of interbody cage 10, cage 10 is coupled to tool 48 by rotating tool 48 to lock it into place using keyed portion 44 and keyed segment 58. When assembled, tool 48 extends through interior 34 of cage 10 and into the distal end 28 of cage 10, allowing superior control over cage 10 during installation.

As shown in FIG. 7, once coupled to tool 48, cage 10 may be inserted into disk space 60. Cage 10 is oriented so that the distal end 28 of cage 10 is inserted first, with the insertion faces 12, 14 facing the adjacent vertebrae 62, 64. As shown in FIGS. 7-9, the cage 10 may be inserted from the posterior of the patient to one side of the vertebral midline, and positioned within disk space 60 adjacent the previously inserted bone graft material (not shown). As a surgeon applies force to insert cage 10, cage 10 moves anteriorly within disk space 60, and as shown in FIG. 9, cage 10 acts as a self-distracting device, distracting vertebrae 62, 64 as cage 10 moves anteriorly because of the increasing distance between insertion surfaces 12, 14 toward the proximal end 24 of cage 10. This self-distraction feature is intended to eliminate, where possible, the necessity of using additional distraction tools and/or devices as a part of the procedure.

Once inserted, cage 10 may be positioned approximately as shown in FIGS. 7-9 (shown without tool 48 in FIGS. 8 and 9) between the adjoining vertebrae 62, 64. As shown in FIG. 10, tool 48 is then rotated approximately 90 degrees about its longitudinal axis, thereby providing additional distraction to vertebrae 62, 64 and rotating gripping surfaces 16, 18 into contact with the adjoining vertebrae 62, 64. The greater distance between gripping surfaces 16, 18 at the distal end 28 of cage 10 acts both to provide additional self-distraction for cage 10 and to allow the cage 10 to conform to the natural curvature of the spine (e.g., the natural curvature of the spine in the lumbar region).

Figure 13:
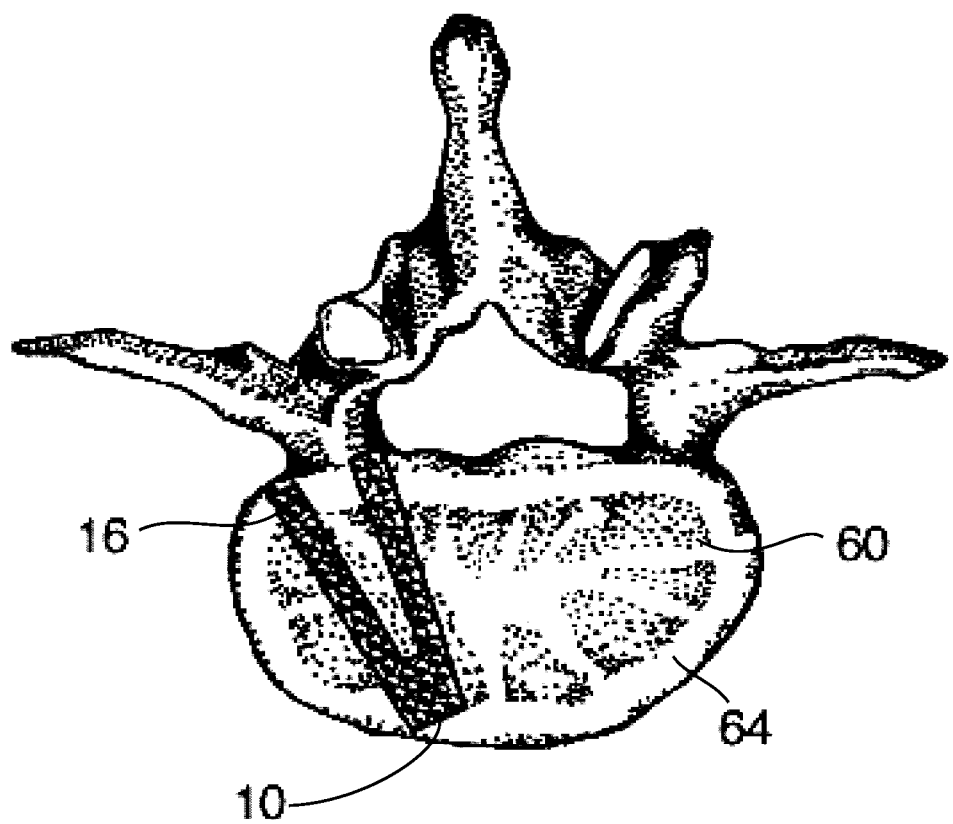
FIG. 13 is a top plan view of the interbody cage of FIG. 9 after removal of the insertion tool, shown within a disk space.

Tool 48 may then be rotated back (i.e., in a direction opposite to that used to lock the tool into place) to unlock tool 48 from keyed portion 44 and tool 48 may be removed from cage 10. Cage 10 will then be oriented substantially as shown in FIGS. 11-13. The "V" shape of cage 10 (see FIG. 13) not only assists in the insertion of cage 10 and initial distraction of the vertebrae 62, 64, but the distance between extensions 30, 32 at the proximal end 24 aids in providing a stable surface for cage 10 that resists tipping after insertion.

After removal of tool 48, the interior 34 of cage 10 is packed with additional bone graft material or bone graft substitute (not shown) as desired to facilitate post-surgical fusion of the adjacent vertebrae 62, 64. A second interbody cage 10 may then be inserted following the above-described methodology, the two interbody cages 10 being situated substantially symmetrically within disk space 60 about the vertebral midline.

Referring to FIGS. 14-16, in an alternative embodiment, the above-described steps may be followed using tool 148. Additionally, prior to installation of interbody cage 10, internal screw 172 is used to further secure tool 148 to cage 10 by passing internal screw 172 through tool 148 and threading internal screw 172 into hole 46 in cage 10. Once cage 10 is positioned and rotated into place, internal screw 172 may be unthreaded and removed from cage 10 and tool 148.

As discussed above, it may also be desirable to deliver fluids, such as bone morphogenic proteins or high dose antibiotics, to disk space 60 after insertion of interbody cage 10. In an exemplary embodiment of the method described herein, and as illustrated in FIGS. 19-22, tool 248 may be provided in a fenestrated configuration (i.e., having openings 282) with delivery device 284. Upon insertion and positioning of cage 10 within disk space 60, internal screw 172 (if used) is removed. As shown in FIG. 20, delivery device 284, shown as a syringe, is then threaded into insertion tool 248. As shown in FIGS. 21 and 22, fluids may then be delivered via syringe 284, through fenestrated tool 248 and cage 10, and into disk space 60. As discussed above, aperture 42 in cage 10 facilitates communication between the interior 34 and the remaining disk space 60 in applications such as the delivery of fluids. Upon completion of the delivery process, the syringe or other delivery device 284 is unthreaded from tool 248, tool 248 is rotated to unlock keyed segment 258 from keyed portion 44, and tool 248 is removed from cage 10. Additional bone graft material or bone graft substitute may then be packed into cage 10 and disk space 60.

It may also be desirable to remove the interbody cage after insertion. Cage 10 and tool 48 (or tool 148 or 248) are configured to facilitate removal of cage 10 after insertion. When cage 10 is coupled to tool 48, the keyed portion 44 and keyed segment 58 interlock so as to enable a surgeon to apply the necessary force required to remove cage 10 from an intervertebral space. This is an advantage over many traditional interbody cages, which do not provide an adequate interface between the tool and the cage to allow for easy removal of the cage from an intervertebral space when necessary.

It may also be desirable to be able to insert an interbody cage into a disk space without having to further rotate the cage once positioned. In an alternative embodiment of the present invention (not shown), the interbody cage may be inserted using the methods described herein, except that the cage is not rotated once positioned within the disk space. The insertion surfaces then also act as the gripping surfaces, and may be provided with appropriate surface textures (similar to gripping members 40) configured to allow the insertion surfaces to grip the vertebral bodies once the cage is installed.

While the detailed drawings and specific examples given herein describe various exemplary embodiments of the invention, they serve the purpose of illustration only. It is to be understood that the invention is not limited in its application to the details of construction and arrangements of components set forth in the preceding description or illustrated in the drawings. It should be noted that the components and/or assemblies of the interbody cage system may be constructed of various materials known in the art. Further, while several examples show the invention in the context of a specific spinal region, the invention is applicable to surgical procedures involving other suitable regions of the spine not described in the embodiments contained herein. Further, the order of performance of the method steps described with respect to spinal fusion procedures utilizing the various embodiments of the present invention may vary. Furthermore, other substitutions, modifications, changes, and omissions may be made in the design, operating conditions, and arrangements of the exemplary embodiments without departing from the scope of the invention as expressed in the appended claims.

What is claimed is:

1. A system for delivery of a fluid to a space between two vertebrae, comprising:
    an interbody cage having an opening providing a pathway between an interior of the cage and the exterior of the cage; and
    a tool having a proximal end and a distal end, the distal end configured to be coupled to the cage, the tool comprising a passage extending from the proximal end to the distal end and an opening near the distal end providing a pathway between the passage and the exterior of the tool;
    wherein the tool opening and the cage opening may be sufficiently aligned to permit the delivery of fluid from the tool, through the cage, to the space between two vertebrae, and
    wherein the tool further comprises a keyed segment and the interbody cage comprises a keyed portion,
    wherein the keyed segment and keyed portion are configured to connect the tool to the cage such that, when connected to the cage, the tool extends past a proximal end of the cage and into an interior of the cage.

2. The system of claim 1, further comprising a fluid delivery device configured to be coupled to the tool to deliver the fluid to the tool passage.

3. The system of claim 2, wherein the fluid delivery device is cannulated and sized to be received within the tool passage, the cannulated portion of the fluid delivery device providing a fluid delivery pathway from the proximal end to the distal end of the tool.

4. The system of claim 3, wherein the delivery device comprises a syringe.

5. The system of claim 2, wherein the delivery device comprises a first threaded portion and the tool comprises a second threaded portion configured to mate with the first threaded portion to secure the delivery device to the tool.

6. The system of claim 1, wherein the fluid is a paste.

7. The system of claim 1, wherein the fluid comprises a bone morphogenic protein or an antibiotic.

* * * * *